United States Patent [19]
Epley

[11] 4,060,701
[45] Nov. 29, 1977

[54] METHOD FOR TESTING ACOUSTICAL ATTENUATION OF HEARING PROTECTORS

[75] Inventor: John M. Epley, Portland, Oreg.

[73] Assignee: Hearing Evaluation & Acoustic Research, Inc., Portland, Oreg.

[21] Appl. No.: 613,245

[22] Filed: Sept. 15, 1975

[51] Int. Cl.² .............................................. H04R 29/00
[52] U.S. Cl. .................................... 179/175; 179/1 N; 179/156 R
[58] Field of Search ................ 179/175, 175.1 A, 1 N, 179/1 P, 156 R, 184; 181/129, 130

[56] References Cited

U.S. PATENT DOCUMENTS

| | | | |
|---|---|---|---|
| 3,729,598 | 4/1973 | Tegt | 179/175.1 A |
| 3,784,745 | 1/1974 | Stearns | 179/1 N |
| 3,906,158 | 9/1975 | Lake | 179/1 N |
| 3,968,334 | 7/1976 | Padilla | 179/175 |

OTHER PUBLICATIONS

Acoustical Society of America Standard 1-1975; published by American Institute of Physics, adopted 8-14-74.

*Primary Examiner*—David L. Stewart

*Attorney, Agent, or Firm*—Chernoff & Vilhauer

[57] ABSTRACT

A method for rapidly and accurately measuring the acoustical attenuation effectiveness of various personal hearing protection devices as worn, particularly in-the-ear type protectors under conditions of normal fit in a working environment having significant ambient noise. The method comprises presenting an audio signal to an ear both with and without the hearing protector in place and noting the difference in intensity of the applied signal, measured in decibels, required to obtain the same perceived amplitude level in each case. The perceived amplitude level may be either the threshold of the subject's hearing perception or a supra-threshold reference point determined by a comparison of the test ear signal with a reference signal in the contralateral ear to allow for testing in ambient noise levels of high or fluctuating intensity. The test signal is preferably a multi-frequency complex signal having a preweighted power spectrum which emphasizes those frequencies which are particularly hazardous. The preferred supra-threshold test utilizes a reference signal in the non-test ear which is audibly distinguishable from the signals applied to the test ear other than with respect to amplitude.

5 Claims, 7 Drawing Figures

METHOD FOR TESTING ACOUSTICAL ATTENUATION OF HEARING PROTECTORS

BACKGROUND OF THE INVENTION

The present invention is related to a system for measuring the acoustical attenuation effectiveness of devices employed to protect the hearing of workers subjected to relatively high levels of ambient noise.

Various types of hearing protection devices are in current use to protect the hearing of an individual working in an environment having a high ambient noise level. Generally, these hearing protection devices fall into two broad categories: earmuffs, which fit over and around the ears; and earplugs, which fit into the ear canal. Not only is there a substantial variation in the acoustical effectiveness of the different types of hearing protection devices, i.e., their ability to adequately attenuate the sound pressure level of certain hazardous noises to which the ear is exposed, but there is also a substantial variation in the effectiveness of single models of the same type, principally because of the variation in "goodness of fit." A slight defect in fit can render the protective device virtually ineffectual, thereby exposing without warning the ears of the wearer to hazardous ambient noise having frequencies and amplitudes sufficient to cause a gradual, painless and therefore often unnoticed permanent loss of hearing. All too often the ineffectiveness of a particular hearing protector is not detected until there has been a permanent impairment of the user's hearing.

At the present time, the most widely used means for monitoring the true effectiveness of hearing protection devices is to measure an individual's hearing level with a conventional audiometer at intervals of six months or more to determine if a permanent loss of hearing has occurred. Such audiometric monitoring, however, besides having the disadvantage of being "after the fact," is incapable of providing the information necessary to permit differentiation between those individuals who have sustained a hearing loss due to inadequate protection and those who have sustained losses due to other causes such as infectious disease, degenerative disease, and the like. This inability of present monitoring means to differentiate between work-caused hearing losses and those suffered from other causes has many medico-legal ramifications for both the worker who has suffered a hearing loss while working in a high-noise environment and for his or her employer.

Various means have been devised for objectively testing the acoustical effectiveness of muff-type hearing protectors. See, for example, Tegt U.S. Pat. No. 3,729,598 and a paper entitled "Method for the Measurement of Real-Ear Protection of Hearing Protectors and Physical Attenuation of Ear Muffs, ASA STD 1-1975" available from the Acoustical Society of America, 335 East 45th Street, New York NY 10017. The latter reference also includes a description of a method for subjectively testing the effectiveness of plug-type hearing protectors in a noise-free environment, such as found in a soundproof booth or test room, and employing a plurality of spaced loudspeakers to produce a free-field test signal.

The only presently accepted methods of testing ear protection devices, including the methods disclosed by the aforementioned paper of the Acoustical Society of America, require that the individual be placed in an ambient noise-free environment such as a soundproof booth and subjected to a series of free-field test tones at different frequencies and amplitudes to determine his acoustical threshold level with the hearing protection devices in place (occluded threshold) and his acoustical threshold level with the hearing protection devices removed (open threshold), and then comparing the occluded and open threshold level amplitude measurements to determine the acoustical attenuation provided by the hearing protectors. These methods, because they do not test each ear and thereby each of a pair of hearing protectors separately, while helpful in determining the attenuation provided by the worst of the two protectors or the protector positioned in or around the better of the subject's two ears, are not capable of indicating which of the protectors or which of the ears is being tested. Moreover the requirement for testing in an ambient-noise free environment requires physically removing the subject from his working environment which is time-consuming and therefore costly, and limits as a practical matter the frequency with which such tests can be conducted.

Furthermore, after the individual's occluded and open threshold levels have been measured at different frequencies and the attenuation provided by the hearing protector has been calculated for each frequency, the attenuation calculations must still be weighted according to the noise spectra of the work environment and the relative hazard of the different frequencies. These calculations and weighting are both complicated and time consuming.

Accordingly, the known prior art methods for measuring the attenuation provided by hearing protection devices are infeasible and uneconomic for general field use and must of necessity be restricted almost exclusively to use in the laboratory for developing data regarding the acoustical effectiveness of specific models of hearing protectors. No convenient method has yet been devised to measure the attenuation effectiveness of a particular hearing protector while it is in place in the ear of the user under normal conditions of fit at his workplace. Thus, even though a particular type of hearing protector may function effectively during a laboratory-type test, there is no guarantee that it will function effectively when worn by persons other than the individual tested in a laboratory and under other than laboratory-type conditions. Consequently, a worker who requires adequate noise protection against hazardous ambient noise has no way of knowing if his hearing protection is really failing until he has suffered a permanent measurable loss of hearing.

SUMMARY OF THE INVENTION

The present invention is directed to a system for measuring the acoustical attenuation effectiveness of hearing protectors, especially those adapted to be worn in the ear canal. More particularly, the present invention comprises a system for rapidly and subjectively measuring the acoustical attenuation provided by in-the-ear type hearing protectors or earplugs as normally worn by a particular individual at or near the individual's work station and without requiring the use of a low-noise or quiet-room type environment. As used herein, the term "earplug" is understood to include hearing protectors worn within the external acoustic meatus or ear canal as well as those worn in the concha distal to the extrance to the external ear canal.

The method of the present invention, as applied to earplugs, comprises two independent alternative tests for determining the acoustical effectiveness of earplugs under differing conditions of ambient noise: the threshold test and the supra-threshold test. The threshold test is used to measure earplug effectiveness under no-noise or non-fluctuating noise conditions, and the supra-threshold test is used to measure earplug effectiveness in the presence of relatively high or fluctuating ambient noise. In both tests, the earplug wearer can be tested at or near his or her work station, preferably without advance notice to ensure that a true measurement of the acoustical effectiveness of the earplug is obtained as the earplug is normally worn and not as the earplug is specially fitted by the wearer in anticipation of being tested. The test may also be performed at the time that an earplug is initially fitted to ensure that a correct fit is obtained. In the preferred practice of both tests as applied to earplugs, a pair of transducer-equipped earcups are placed over the ears of the subject to attenuate ambient noise and expose the test ear to a test audio signal. The earcups are specially adapted to completely surround the ear and the adjacent sound-transmitting bone structure of the skull without contacting or otherwise disturbing the placement of the earplugs.

Alternatively, the threshold test may be performed by transmitting a test signal to the subject individual's ears as a free-field signal via one or more spaced loudspeakers. In the latter instance, both earplug- and earmuff-type hearing protectors may be tested, but not in the presence of ambient noise; moreover, to enable the speaker to direct the signal to each ear separately to measure the acoustical effectiveness of each individual hearing protector, additional attenuation in the form of an earplug or ear muff must be added to the untested ear prior to the test.

To begin the threshold test, a test signal is transmitted to the test ear with the hearing protector in place, and the amplitude of the signal is alternately decremented and incremented until the subject indicates that the signal is at his auditory threshold level. As used in the disclosure and claims, the subject's auditory threshold level is intended to include the amplitude of the test signal at the point where it becomes barely audible to the subject, or alternatively the point where it becomes barely inaudible, the only requirement being that the particular method of determination used be consistently employed throughout the testing procedure. Since the amplitude of the test signal can be detected and fixed regardless of which method of determination is employed, the amplitude is referred to herein as "perceptible" to the subject even though it may be barely inaudible to him.

The threshold level is noted by an appropriate numerical indication of relative amplitude in logarithmic units, and the test is repeated on the test ear without the hearing protector in place. The difference between the two resultant numerical indications of relative amplitude represents a measurement of the acoustical attenuation effectiveness of the protector.

It is not necessary for the purposes of the present invention that the auditory threshold level of the individual in each case be calibrated to a standard scale as is done in audiometric testing, since it is the difference between two relative amplitude levels that is used to determine the acoustical effectiveness of the hearing protector being tested. It is only necessary that the numerical indications be such that their difference accurately represents the difference in amplitude between the respective test signals, expressed in appropriate units such as decibels. It is understood, however, that the auditory threshold level of the subject could be calibrated to a standard scale during the performance of the present method without departing from the invention as conceived and disclosed.

The actual decrementing and incrementing of the test signal amplitude is accomplished by either the subject or the test operator manipulating a small, simple, hand-held control unit, such as a two-position toggle switch or push-button. If the test operator manipulates the control unit, the subject indicates the points where the test signal becomes barely inaudible or audible by hand signals or other means.

To obtain an accurate indication of the subject's auditory threshold level in both the open and occluded phases, the test signal is decremented and incremented a number of times in succession and the respective points at which the signal is perceived to be at the threshold level are then noted by means of respective numerical indications and averaged to provide an average numerical indicator of the threshold amplitude level. In practice, it has been found that an acceptably accurate indication of an individual's threshold level in either phase can be obtained by decrementing and incrementing the amplitude of the test signal six times, taking a reading of the threshold level during each of the last three sequences and then averaging these three readings to arrive at the relative numerical indication of threshold amplitude. By effectively discarding the first three of the six readings, the resultant average threshold numerical indication is not affected by false indications taken while the individual is still becoming accustomed to the test procedure.

It will be noted that, although the foregoing method of the present invention utilizes the hearing response of the subject individual to obtain a measurement of the acoustical effectiveness of the hearing protector, the presence of a partial unilateral or bilateral hearing loss does not invalidate or significantly distort the test results. This is because each phase of the test, occluded and open, involves only one independent variable, the protector itself, and in calculating the auditory threshold differences described above the non-variable factors such as hearing loss are effectively cancelled out.

A correctly fitted hearing protector should provide approximately 20 db or greater attenuation of the most harmful frequencies of the noise spectrum. A particular advantage of the present invention is that, if less attenuation is measured, the protector fit may be adjusted on the spot and its effectiveness remeasured. If still failing, the protector may be replaced and a new protector tested. Where earplugs are involved, this may all be accomplished without requiring the individual to leave his or her work station or to be "off the line" for more than a few minutes. In addition, the individual may be reoriented as necessary to correct any fitting problems not resulting from protector design.

To facilitate the discernment of the test signal by the subject individual when testing earplugs in a noisy environment, a separate masking noise may be transmitted to either or both earcup transducers to minimize the distracting effect of ambient noise. The most effective masking noise has been found to be that having a quality similar to ambient noise, for example a complex signal comprising substantially all of the audio frequencies at substantially equal amplitudes. Such a signal is well-known in the art as white noise.

In those circumstances where earplugs are to be tested in the presence of ambient noise of high or fluctuating intensity, the second basic test of the present invention, the supra-threshold test, is employed. This test is basically similar to the threshold test described above but includes the additional step of transmitting a reference signal to the non-test ear of the subject while simultaneously transmitting the test signal to the test ear. The reference signal is maintained at a constant audible amplitude sufficient to effectively mask the ambient noise, that is, to be audible over the ambient noise. Rather than utilizing the auditory threshold level of the subject as the reference point in both the occluded and open phases, however, the subject is asked to compare the varying test signal to the reference signal in each phase and indicate the points where the test signal is perceived as having a predetermined common or consistent relationship to the reference signal in each phase. This relationship, which determines the reference point, may be the point where the test signal amplitude balances that of the reference signal, or alternatively where the test signal is barely louder or softer than the reference signal, or some other detectable relationship. Again, it is necessary only that the relationship used be consistent throughout the test and be detectable by the subject. Test signal amplitude indications at the reference point in each phase are obtained and averaged as with the threshold test, and the results differenced to obtain the acoustical attenuation effectiveness. Note that even though the respective amplitude level indications obtained from the supra-threshold test are higher than those obtained by the basic threshold test, the difference between the respective indications with the protectors in place and with the protectors removed will be substantially the same, as the only difference between the indications in either case is the acoustical attenuation provided by the protectors. Thus, the use of the supra-threshold test permits a measurement of the acoustical attenuation effectiveness of an earplug to be readily obtained even in a high-noise or fluctuating noise environment without requiring that the subject be transported to a low-noise or noise-free environment, and thereby permits the effectiveness of the earplugs to be tested more frequently without the lengthy period of worker absence inherent with known prior art methods employing a conventional audiometer and a soundproof booth or room.

To obviate the need to calculate the difference between the occluded and open readings of relative amplitude in either the threshold test or the supra-threshold test, an indicator responsive to the amplitude of the test signal may be set to zero as a base setting at the threshold or reference point level in the occluded phase. When the protector is removed and the threshold or reference point level re-indicated, the indicator then indicates directly the numerical difference between the two levels and provides a direct measurement of the acoustical attenuation effectiveness of the protector. Alternatively, an automatic calculator function could be included in the system to perform the function of calculating the difference between the above-described numerical indications, and also to perform the above-described averaging of multiple readings.

The signal used as the test signal of either test, and the reference signal of the supra-threshold test, may be a pure tone comprising a single audio frequency or a complex signal comprising several frequencies in the audio range, and either continuous in duration or pulsed. If a pure tone is used, a series of tests are usually taken at different frequencies and the results then adjusted or weighted according to the relative hazard represented by the various frequencies to the human ear. To obviate the need to take a series of measurements at different frequencies and then weight the results, the preferred method of the present invention utilizes a preweighted signal comprising a complex multi-frequency noise signal having the amplitudes of preselected frequency components adjusted according to their relative hazard; that is, the power spectrum of the signal is more weighted in the audio frequency range above 1000 Hz than below 1000 Hz, and is preferably weighted in accordance with a standard A-frequency weighting. By using such a complex pre-weighted multi-frequency test signal, the test need be performed only once to obtain approximately the same weighted results that are obtained by using a single pure-tone test signal or narrow band signal and performing the test a number of times at different frequencies. Besides decreasing the amount of time required to perform the test, the use of a preweighted multi-frequency test signal also reduces the amount of time required to obtain the numerical test results once the test has been completed and eliminates the possibility of human error attendant with the manual weighting calculation of the individual test measurements resulting from a series of pure-tone tests. In the supra-threshold test, both the reference signal and the test signal may be pre-weighted complex signals to facilitate their ready comparison by the subject. In either test, the test signals can be pre-weighted in only one of the occluded and open phases of the test to obtain other forms of measure of attenuation effectiveness. However, similarly weighting the signals in both phases simplifies the audio signal generation apparatus.

Although signals of identical continuous or pulsed character may be employed as the test and reference signals in the supra-threshold test, best results are obtained when using pulsed signals with the test and reference pulses respectively being audibly distinguishable with respect to time. In particular more accurate results are obtained if the reference signal and the test signal are presented to the subject as respective periodic pulse trains having asymmetrical timing to permit the subject more easily to lateralize the signals. Moreover there should be a substantial overlap between the durations of the respective test and reference pulses; that is, the test pulse should begin before the reference pulse ends and/or vice-versa. This overlapping of the pulses of the two signals has been found to be particularly effective in minimizing the tendency for the consecutive reactions of the subject to drift as the amplitude of the test signal is alternately decremented and incremented; that is, the overlapping tends to prevent the subject from perceiving the increasing loudness of the test signal as a greater than actual loudness before it has reached a truly greater loudness by producing a stabilizing period during each signal overlap. Stated another way, the overlapping reinforces the effect of the signal having the greater loudness.

The preferred apparatus of the present invention comprises a hand-held, battery-powered, portable electronic test unit, a pair of specially adapted headphones and a remotely operable, hand-held two-position control switch. Means are provided within the test unit for producing the complex multi-frequency test signal, weighting the power spectrum of the signal according to the relative hazard of its constituent frequencies, and amplifying the signal to an audible level. Means are also provided for digitally controlling the amplitude of the signal in response to the operation of the hand-held control switch, one position of the switch causing the amplitude to increase and the other position of the switch causing the amplitude to decrease. The control switch itself is preferably a two-position switch and may be a single push-button, a pair of push-buttons, a toggle switch or a combination thereof.

The headphone set forming a part of the apparatus of the present invention comprises a pair of earcups, each of which is specially shaped to fit around one of the subject's ears encompassing both the ear and the sound-transmitting portion of the skull surrounding the ear. An audio frequency transducer is positioned in each earcup at a depth sufficient to permit the earphones to be placed over the subject's ears without touching or otherwise disturbing any earplugs being worn by the individual, and to transform the reference and test signals from the test unit into sound pressure waves. Each transducer is resiliently (i.e. non-rigidly) mounted to an earcup so as to prevent transmission of sound from the transducer through the cup to the skull, which would otherwise produce an unwanted degree of bone conduction and thereby introduce possible error in the test.

In operation, for example to perform the threshold test, the earcups are placed over the ears of the subject while his earplugs are in place, the noise circuit of the test unit is activated to produce the multi-frequency test signal which is then weighted and fed through the digitally controlled attenuator circuit and a power amplifier circuit to one of the transducers in the headphones. When the two-position hand-held control switch is in one position, an internal digital control circuit automatically activates a digital counter circuit to decrement the amplitude of the test signal in successive steps of preselected amount via the digitally controlled attenuator circuit. When the control switch is placed in the other position, the amplitude of the test signal can be automatically incremented in similar successive steps. Thus, by performing the task of moving the control switch from one position to the other, the subject or the test-unit operator may decrement and increment the amplitude of the test signal between an audible and an inaudible level.

For the supra-threshold test, the activation of another switch causes the same complex weighted signal to be fed through a separate power amplifier, bypassing the digitally controlled attenuator, to the transducer in the opposite earcup thereby exposing the non-test ear to a constant-amplitude reference signal. In this latter case, the two-position movement of the control switch decrements and increments the amplitude of the test signal with respect to the constant-amplitude reference signal. Separate control switches on the test unit selectively switch the reference and test signals from one ear cup transducer to the other, and provide selection of alternate amplitude levels of the reference signal.

By employing separate earcups and transducers to both attenuate the ambient noise and to transmit the test signal to the particular ear being tested, each ear and thereby each earplug is tested separately, an achievement not heretofore practiced with systems employing a quiet room and one or more spaced loudspeakers. This feature of the present invention is especially important when testing an individual having less than substantially equal hearing ability in both ears.

It is, therefore, a principal objective of the present invention to provide a simple, efficient and inexpensive system for measuring the acoustical attenuation effectiveness of in-the-ear type hearing protectors without requiring the use of a sound-proof environment and preferably without disturbing the initial placement of the protectors.

It is an additional objective of the present invention to provide a system for measuring the acoustical attenuation effectiveness of in-the-ear type hearing protectors in the presence of relatively high levels of ambient noise.

It is a further objective of the present invention to provide a system for measuring the acoustical attenuation effectiveness of each of two hearing protectors individually and separately.

It is a still further objective of the present invention to provide a system of measuring the acoustical attenuation effectiveness of hearing protectors utilizing as a test signal a complex multi-frequency noise signal, the power spectrum of which is preweighted according to the relative hazard to the human ear of its constituent frequencies to obviate the need to similarly weight the separate results of a series of measurements each utilizing a different frequency pure-tone test signal.

The foregoing objectives, features and advantages of the present invention will be more readily understood upon consideration of the following detailed description of the invention taken in conjunction with the accompanying drawings.

DETAILED DESCRIPTION OF THE PREFERRED EMBODIMENT METHOD

The method employed in the present invention comprises two basic tests for determining the acoustical attenuation effectiveness of hearing protectors, principally those fitting into or adjacent the external opening of the ear canal, without disturbing the fit of the hearing protectors as they are worn and without requiring the use of a sound-proof environment. The two basic tests are (1) the threshold test for use under non-fluctuating noise conditions and (2) the supra-threshold test for use in the presence of relatively high or fluctuating levels of ambient noise. Each test is founded on the premise that the acoustical attenuation provided by a hearing protector with respect to a given ear may be determined by measuring the amplitude difference between an audio signal perceived by that ear with the hearing protector in place, and an audio signal perceived, without the hearing protector, as corresponding to the amplitude of the first signal. As used herein, "audio signal" is intended to include broadly both sound waves transmitted to the ear and electrical signals transmitted to an audio transducer which produces such sound waves.

To start the threshold test, a subject with his hearing protectors, for example earplugs, operatively in place is approached at his work station preferably before the subject has a chance to adjust or otherwise affect the fit of his earplugs. A pair of transducer-equipped earcups are placed over the subject's ears to encompass not only the ears and the earplugs but also the immediately adjacent sound-transmitting portion of the skull. The earcups used should be specially adapted to have their audio transducers set well back within the individual earcups to avoid touching or otherwise disturbing the placement of the earplugs. An audio signal is transmitted to the transducer in the earcup surrounding one of the subject's ears, for example the left ear, through the earplug. An indication of the auditory threshold level of the left ear with the earplug in place, defined as the occluded threshold level, is obtained by alternately decrementing the amplitude of the test signal until it becomes inaudible and incrementing it until it becomes just barely audible. A numerical indication representing the amplitude of the test signal at the point wherein it becomes barely inaudible to the subject is recorded or otherwise saved as representing the occluded auditory threshold level. The test signal is then switched to the transducer located in the earcup surrounding the other or right ear and the procedure repeated with that earplug in place. The earplugs are then removed from both ears and the procedure repeated to obtain numerical indications of the amplitudes of the test signal at the points where it becomes barely inaudible to the left and right ears respectively with the earplugs no longer in place. These latter amplitudes represent the open auditory threshold level of each ear. The acoustical attenuation provided by each earplug is obtained by comparing the numerical representations of the occluded auditory threshold level and the open auditory threshold level of each ear individually; that is by subtracting the numerical representation of the open auditory threshold level of the left ear from the occluded auditory threshold level of the left ear to obtain a numerical representation of the attenuation effectiveness of the earplug originally positioned in the left ear, and performing a similar comparison for the right ear to obtain the audio attenuation effectiveness of the earplug originally positioned therein.

An alternative method of performing the threshold test is, of course, to take both the occluded and open threshold readings for a single ear before taking corresponding readings for the opposite ear.

Because of the time required for an individual to become accustomed to recognizing the test signal, and more particularly the point at which the amplitude of the test signal passes from an audible level to a level that is barely inaudible (or vice-versa if barely audible readings are taken in both phases), a more accurate indication of the acoustical attenuation provided by the hearing protectors is obtainable by decrementing and incrementing the amplitude of the test signal a number of times in sequence during each auditory threshold determination, discarding the first few readings to permit the individual to become accustomed to the test and then averaging a predetermined number of subsequent readings to obtain a numerical indication of the particular auditory threshold level. For example the preferred method includes, for each threshold determination, alternately decrementing and incrementing the test signal a total of six times to obtain six readings. Each of the first three readings is ignored and each of the next three successive readings is noted. The three threshold indications so obtained are then added and divided by three to obtain an average numerical indication of the particular auditory threshold level being determined. It is understood however that more or less than six readings, and a greater or lesser percentage of the readings, may be averaged to produce the final result without departing from the principle as disclosed provided that the procedure of discarding early readings in favor of later ones is followed.

Under conditions of relatively high or fluctuating ambient noise the subject may undergo a significant shift in the level which he perceives as being his threshold under the threshold test. Under such conditions the acoustical effectiveness of the earplugs worn by the subject may still be tested at or near the individual's work station and without requiring the use of a noise-free environment by utilizing the supra-threshold test of the present invention whereby a second or reference signal is transmitted to one ear of the subject while the test signal is transmitted to the other ear. In this embodiment of the present invention, transducer-equipped earcups are placed in position about the ears of a subject earplug wearer as before with both earplugs in place, and a reference signal is transmitted to one of the transducers (i.e. the non-test ear) at a constant amplitude level that is audible to the subject through the earplug over the ambient noise. A test signal is then transmitted to the transducer proximate the opposite ear (the test ear) and its amplitude is decremented and incremented to obtain a numerical representation of its amplitude at the point where it is perceived by the subject as having a predetermined detectable relationship to the constant reference signal. This relationship, which determines the test signal reference point, may be the point where the test signal amplitude balances that of the reference signal, or where it becomes slightly louder or softer, depending on the point which is easiest for the subject to detect with consistency. Once a particular relationship for determining the reference point is selected, however, it must be used consistently in both the occluded and open phases of the test ear.

The recommended sequence for supra-threshold testing is as follows:

A. With both plugs in place, the variable test signal is presented to the right ear (the test ear) and the fixed reference signal is presented to the left. Appropriate readings are taken at the reference point, as perceived and signaled by the subject.

B. The right plug is removed, and the same test procedure carried out.

C. The test and control signals are reversed, and a corresponding test procedure is carried out on the left ear (now the test ear), leaving the plug in the left ear only.

D. The left plug is removed and the same test procedure is repeated.

In the C and D portions of the test, the reference signal is ideally set at a lower level because the non-test ear is unplugged. The attenuation of the right plug is equal to the difference between the A and B readings. The attenuation of the left plug is equal to the difference between the C and D readings.

Alternatively, the constant-amplitude signal can be transmitted to the test ear while the variable signal is transmitted to the non-test ear with the same results. Accordingly such reversal of the signals in the supra-threshold test is also intended to be within the scope of the present invention.

In both the threshold test and the supra-threshold test, it is preferred for reasons previously described that the test and reference signals comprise a complex broadband signal of multiple frequencies in the audio range having the amplitudes of preselected frequency components adjusted according to their relative hazard; that is, the power spectrum of the signal is more "weighted" (i.e. has a higher positive amplitude) in the audio frequency range above 1000 Hz than below 1000 Hz. Ideally, the preferred weighting of the complex test signal follows essentially that known in the industry as A-frequency weighting, an example of which is given in the following table using 1,000 Hz as a reference.

A-FREQUENCY WEIGHTING

| Frequency (Hz) | Weighting (db) |
|---|---|
| 125 | −16.1 |
| 250 | −08.6 |
| 500 | −03.2 |
| 1000 | −00.0 |
| 2000 | +01.2 |
| 4000 | +01.0 |
| 8000 | −01.1 |

Besides using a preweighted test signal, the preferred method of the present invention also includes forming the test signal into a series or train of sequential pulses wherein the interval between each successive pulse is substantially less than the duration of the pulse itself. The use of a pulsed test signal results in a more accurate determination of the various amplitude levels as the subject is more readily able to discern a pulsed signal from relatively continuous externally generated ambient noise and internally generated physiological noise, the latter known more commonly as a ringing in the ears or tinnitus.

In the supra-threshold test, both the test signal and the reference signal are pulsed generally in asymmetrical time sequence with portions of the pulse durations of the respective signals overlapping such that a test pulse begins before the preceding reference pulse ends, and a reference pulse begins concurrently with the end of the preceding test pulse. Without the asymmetrical time sequences of the two signals, it has been found that some subjects experience difficulty in lateralizing the two signals, i.e. determining which signal is being heard by which ear. Without the overlapping of the test signal and reference signal pulses, a subject attempting to compare the amplitudes of the two signals has a tendency to interpret the increasing amplitude of the test signal as a greater than actual amplitude. This tendency on the part of the subject in turn causes the subject's determination of the auditory reference point to drift as the amplitude of the test signal is repeatedly decremented below that of the reference signal and then incremented. By overlapping the durations of the respective pulses a stabilizing period is created between the time a pulse of one signal begins and the preceding pulse of the other signal ends, which reinforces the perception of which signal is truly the loudest and minimizes the problem of drifting reference point determinations.

Although both the threshold test and the supra-threshold test have been described in detail with regard to in-the-ear type hearing protectors, the threshold method may also be performed to obtain an indication of the acoustical attenuation effectiveness of earmuff-type (or earplug-type) hearing protectors by placing the subject in a relatively quiet area and transmitting the test signal to a loudspeaker in both the occluded and open phases of the test ear. The speaker should be maintained at a constant distance from the subject in both phases of the test. To enable the subject to discriminate the test ear from the non-test ear, additional attenuation is added to the non-test ear. For example an earplug and an earmuff together would be worn on the non-test ear while the test ear is in both the occluded and open phases with respect to a single hearing protector being tested.

The actual decrementing and incrementing of the amplitude of the test signal in the threshold and supra-threshold tests is accomplished by either the subject or the test operator's manipulating a two-position, remotely operable control switch, such as a two-position toggle or push-button switch. When the switch is placed in one position, the amplitude of the signal is decremented and when the switch is placed in the other position the signal is incremented. The subject is instructed to indicate the threshold level or reference point as the case may be by actuation of the switch, or by a signal to the test operator who then actuates the switch. Actuation of the switch in one of its two positions, depending on the test method employed, records the above-mentioned numerical indications needed to measure attenuation effectiveness of the hearing protector.

Alternatively, the test signal may be decremented and incremented by the operator or subject's operating a dial or similar amplitude controller that is coupled to a resettable relative amplitude indicator. In the occluded phase the dial is adjusted until the test signal is at the threshold or reference point, and then the indicator is set to zero. In the open phase the dial is again adjusted until the test signal is perceived to be at the same threshold or reference point, while the indicator is allowed to move in response to the adjustment of the dial. The reading of the indicator will now correspond directly to the acoustical attenuation provided by the hearing protector. Thus, by either the operator or the subject's manipulating a single dial it is possible to obtain directly a numerical representation of the acoustical attenuation effectiveness of a hearing protector without the need to calculate the difference by hand between the readings of the occluded and open phases.

It will be noted from the previous disclosure that the preferred method of performing either the threshold or supra-threshold test is to present the test signal to the test ear in the occluded phase first, and thereafter in the open phase. This particular sequence is of course advantageous because it enables the test to be performed without altering the initial fit of the protectors at the time the subject is approached. However in cases where preservation of an initial normal fit is not critical, for example in the initial fitting of earplugs, it is more convenient that the sequence be reversed. Such reversal is included within the scope of the present invention.

Apparatus

Figures 1, 4, 5, 6:
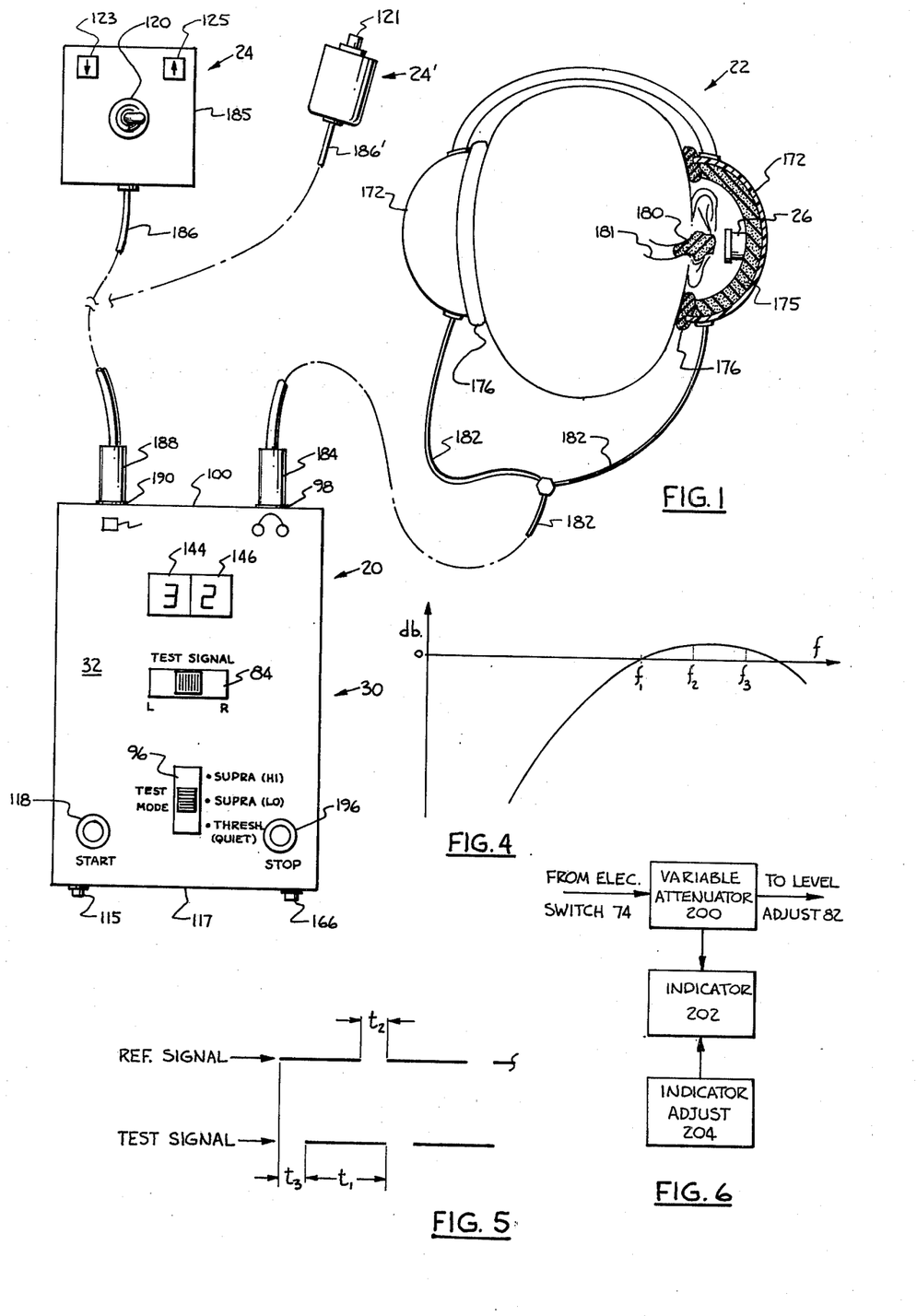
FIG. 1 is a partially extended assembly view of an exemplary embodiment of the apparatus utilized in the system of the present invention.
FIG. 4 is an exemplary power spectrum curve for the pre-weighted test signal utilized in the present invention.
FIG. 5 is a time-sequence diagram depicting the overlapping relationship between the alternating test signal pulses and reference signal pulses utilized in the present invention.
FIG. 6 is a schematic diagram of an alternate electrical attenuator control circuit adapted for the practice of the present invention.

Referring to FIG. 1 of the drawings, the preferred apparatus of the present invention is seen to comprise a portable electronic test unit 20 interconnected with a transducer-equipped headphone 22 and remotely operable control unit 24. The test unit itself comprises an enclosure 30 containing electronic circuitry, partially controllable by the operation of a two-position toggle switch 120 mounted in the enclosure 185 of the remote control unit 24, for producing and selectively transmitting an audio signal separately and interchangeably to either or both of the transducers 26 mounted in each earcup 172 of the headphone 22. If desired, the toggle switch 120 of the remote control unit 24 may be replaced or paralleled by the electrically equivalent two-position push-button switch 121 shown in the figure or by other types of two-position switches. Electrical connection of the remote control unit 24 to the circuitry of the test unit 20 may be by an interconnecting cable 186 and phone plug 188.

Each earcup 172 of the headphone 22 is specially adapted, by having its associated transducer 26 set well back into the recess of the cup, to fit over and encompass an ear of a subject individual without touching or otherwise disturbing a protruding earplug 180 placed in the subject's ear canal 181 as shown in FIG. 1. A conformable, resilient annular sealing member 176 is provided around the tip of each cup and the cups are lined with a resilient sound-absorbent material 175 to reduce the effect of any ambient noise that may be present in the area where the apparatus is being used and to resiliently mount the transducer 26 to the earcup 172 so as to prevent physical conduction of sound from the transducer directly to the earcup. Other types of resilient mountings for the transducer 26, such as flexible rubber grommets, resilient wires, etc. supportively holding the transducer within the earcup 172 would be suitable for the purpose. Electrical connection of each transducer 26 to the circuitry of the test unit 20 may be by an interconnecting cable 182 and phone plug 184.

Figure 2:
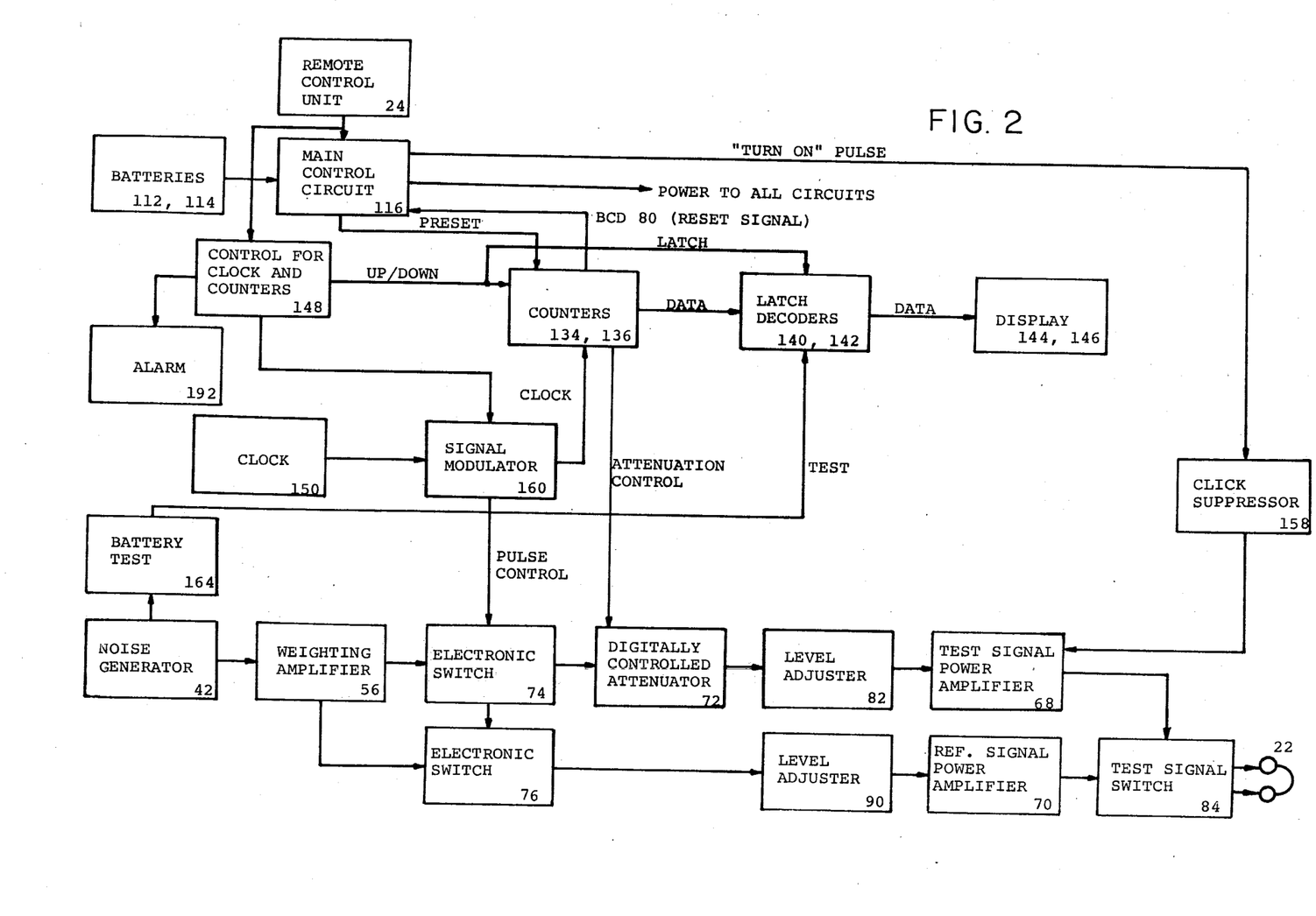
FIG. 2 is a schematic diagram of the major components of the apparatus of FIG. 1.
Figure 3A:
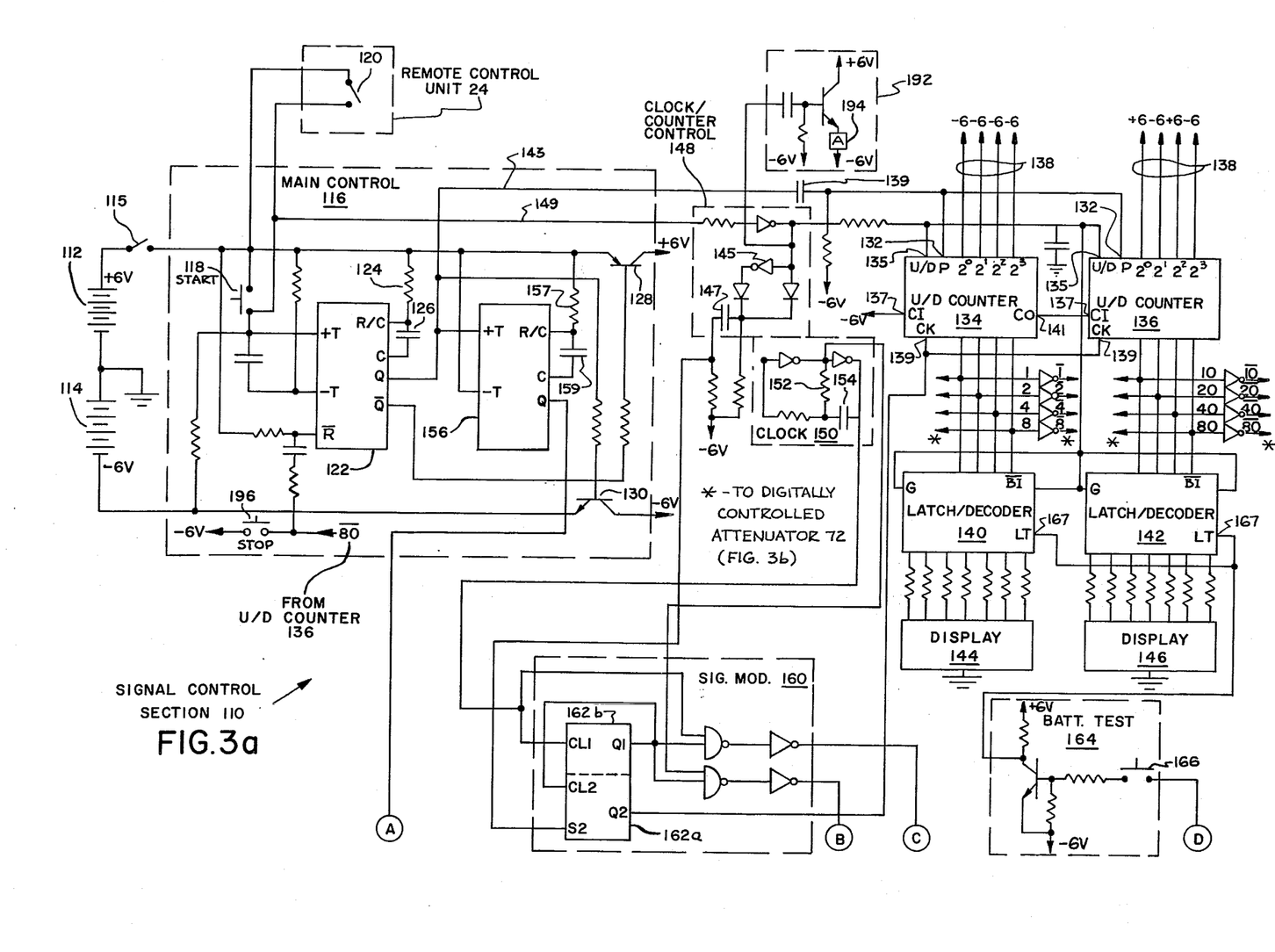
FIGS. 3a and 3b are schematic diagrams of the electrical circuit of the apparatus of FIG. 1.
Figure 3B:
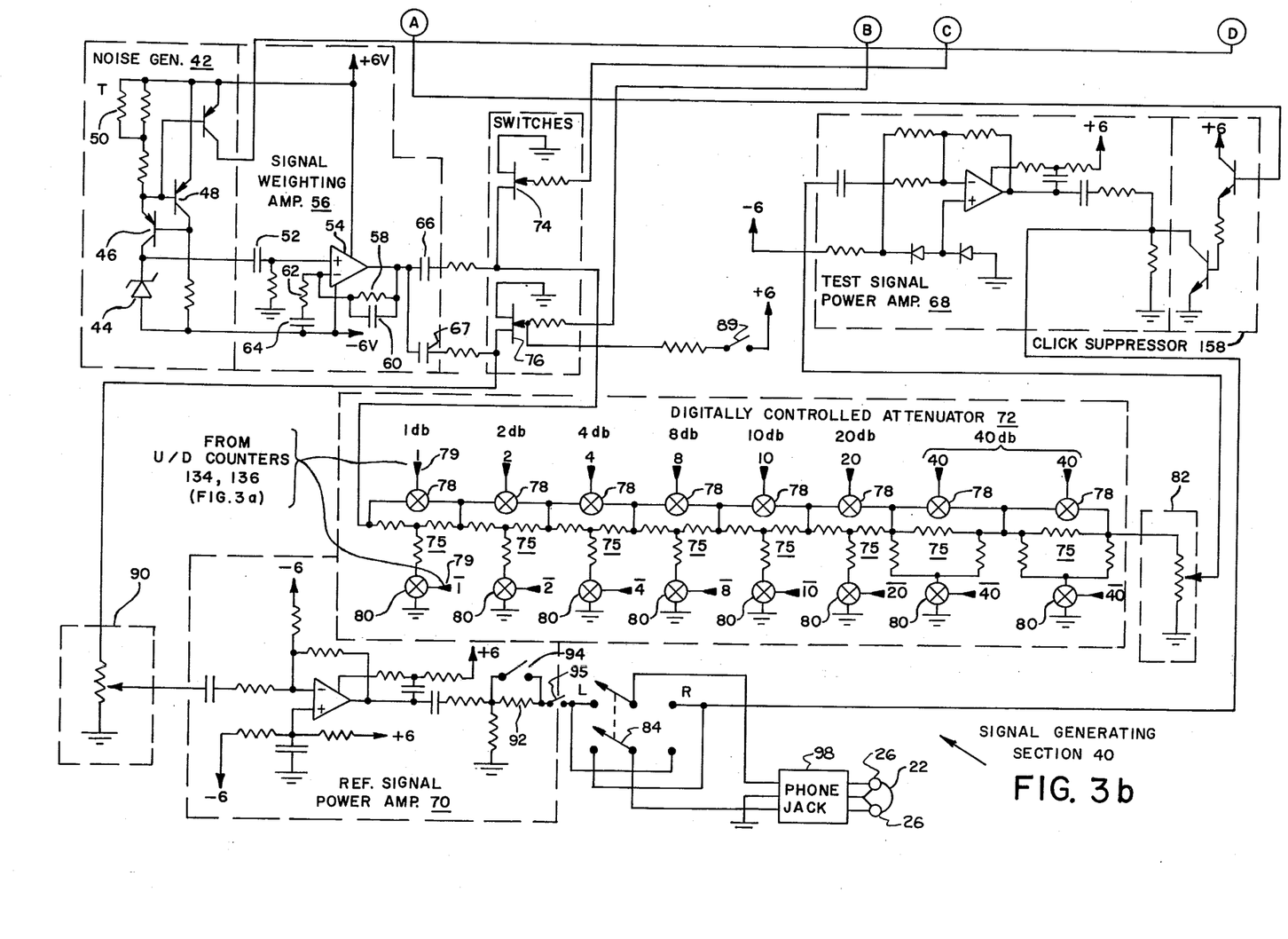

The test unit circuitry, shown in detail in the logic diagram of FIG. 2 and the schematic diagrams of FIGS. 3a and 3b, is best understood if broken down into its two major sections, the signal generating section 40 of FIG. 3b and the signal control section 110 of FIG. 3a. In general, the signal generating section 40 produces an audio signal regulated in time and amplitude in response to logic signals generated by the signal control section 110, and transmits the audio signal to either or both of the transducers 26 of the headphone 22. The operation of the signal control section 110 is in turn regulated by manipulating the toggle switch 120 of the remote control unit 24 or the push-button start switch 118.

Referring specifically to FIGS. 2, 3a and 3b, the signal generating section 40 of the test unit 20 is seen to include a noise generator circuit 42 comprising a Zener diode 44 that is maintained in a reverse breakdown condition at a regulated or controlled current level by the combined action of two interconnected transistors 46 and 48. As is well known to those familar with the art, a Zener diode that is reverse biased sufficient to cause avalance breakdown will generate a multi-frequency noise signal having a relatively flat power spectrum throughout the audio range, a signal of the type generally known as "white noise." This noise signal, the level of which is stabilized with respect to temperature by a thermister 50 compensating the base-emitter junction of the stabilizing transistor 48, is fed through a coupling capacitor 52 to the positive input terminal of an operational amplifier 54 forming the nucleus of a signal weighting amplifier 56.

The weighting amplifier 56 amplifies and shapes the power spectrum of the noise signal so as to produce a complex multi-frequency signal having a power spectrum similar to that shown in FIG. 4. The high frequency roll-off point at $f_3$ of FIG. 4 is determined by the RC time constant of the parallel combination of resistor 58 and capacitor 60 connected to the negative input terminal of the operational amplifier 54, and the low frequency roll-off point $f_2$ is determined by the RC time constant of the series combination of resistor 62 and capacitor 64 also connected to the negative input terminal of the operational amplifier 54. Further low frequency attenuation at $f_1$ (approximately 1000 Hz) is provided by the coupling capacitor 66 connected to the output terminal of the amplifier. Although a multi-frequency signal having a power spectrum other than that shown in FIG. 4 could be obtained by selecting appropriate resistor and capacitor values for the signal weighting amplifier 56, the preferred signal, for reasons discussed earlier, has a power spectrum similar to that shown in the figure and is known generally in the art as an A-weighted signal.

The audio signal from the weighting amplifier 56 is fed in parallel to two substantially identical power amplifiers 68 and 70; to the first or test signal amplifier 68 via a digitally controlled attenuator network 72 and to the second or reference signal amplifier 70 directly. Electronic field effect transistor (FET) switches 74 and 76, one of which is connected to each of the branch circuits emanating from the weighting amplifier 56 are operable as described below to control the signal input to the two amplifiers 68 and 70.

The digitally controlled attenuator 72 interposed between the weighting amplifier 56 and the test signal amplifier 68 comprises a plurality of individual resistive attenuator segments 75, each of which may be selected separately and in combination to attenuate the audio signal passing therethrough from zero to 85 db. For example, selection of the 20 db, 4 db and 1 db attenuator segments provides a total attenuation of 25 db. The 40 db attenuator segment is constructed from two 20 db attenuator segments for ease of realization, with both segments being selectable simultaneously.

Electronic switch circuits 78 and 80 are included in each attenuator segment 75 to selectively switch each segment into or out of the path of the audio signal flowing through the digitally controlled attenuator 72. These switch circuits 78 and 80 are responsive to logic level input signals such that a logical "one" applied to the input terminal 79 of any of the switches will cause the switch to close and conduct, and the application of a logical "zero" will cause the switch to open. As used herein the logic symbol "X" indicates the true value of X or a logical "one" and the logic symbol $\overline{X}$ indicates the complementary or "not" value of X or a logical "zero." Thus, the digitally controlled attenuator circuit 72 of FIG. 3b, the logic symbols 1 through 40 and $\overline{1}$ through $\overline{40}$ adjacent the arrowheads at the input terminals 79 of the switches 78 and 80 indicate that whenever a logical "one" is applied to the input terminal of a switch 78 causing it to close, a logical "zero" will be simultaneously applied to the input terminal of the associated switch 80 causing it to open and vice versa. Accordingly, a single logic signal in its true and complementary forms is utilized to operate each respective switch pair 78, 80 and thereby switch each attenuator segment 75 into and out of the path of the audio signal as the signal flows through the digitally controlled attenuator network 72. Suitable switch circuits are readily available from various manufacturers, for example from Radio Corporation of America (RCA) under its part number CD4066A.

With the digitally controlled attenuator network 72 configured as indicated in FIG. 3b, the amplitude of the audio signal flowing therethrough may be attenuated in 1 db steps from 0 db to 85 db. Additional attenuation or smaller steps may be provided by adding appropriate attenuator segments. At the output of the digitally controlled attenuator 72 the audio signal is fed through a power level adjuster 82 to the input of the test signal amplifier 68 and from there to a double-pole double-throw (DPDT), manually-operable switch 84 that is mounted on the front panel 32 of the test unit enclosure 30 and labeled TEST SIGNAL as shown in FIG. 1. Placing this switch in either the L or R position will transmit the test signal to either the left or right transducer 26 respectively of headphones 22 via a stereophonic-type phone jack 98 mounted as shown in FIG. 1 in the top panel 100 of the test unit enclosure 30.

The audio signal from the weighting amplifier 56 is also selectively fed through a second coupling capacitor 67 and level adjuster 90 to the reference signal amplifier 70 and from there through either a resistor 92 or manually-operable switch 94, and a second manually operable switch 95, to the DPDT TEST SIGNAL switch 84 for selective connection to the transducers 26. The switch 84 is configured as shown in FIG. 3b to transmit the test signal from the amplifier 68 to one of the transducers 26 and the reference signal from the amplifier 70 to the other transducer separately and interchangeably. A manually operable switch 89 connected to the FET switch 76, and the manually operable switches 94 and 95 are ganged together to form the TEST MODE selector 96 mounted as shown in FIG. 1 on the front panel 32 of the test unit enclosure 30. When this selector is in the THRESH (QUIET) position, switch 89 is closed, causing the FET switch to effectively ground the input of the reference signal amplifier 70, and switches 94 and 95 are open, thereby sending the audio signal from the weighting amplifier 56 to the test signal power amplifier 68 only. By grounding the input of the reference signal amplifier 70 and opening its output, not only is the amplifier prevented from feeding a signal to switch 84, but it is also prevented from generating a signal of sufficient amplitude to contaminate the DC power circuitry and thereby affect the signal transmitted by the test signal amplifier 68.

When the selector 96 is in the SUPRA (LO) position, switch 89 is open, removing the ground from the input to the reference signal amplifier 70, and switch 94 is still open and switch 95 is closed, sending the audio signal to both the test signal amplifier 68 and the reference signal amplifier 70 with the reference signal being attenuated by a predetermined fixed amount as it passes through the resistor 92 connected to its output terminal. When the selector 96 is in the SUPRA (HI) position, switch 89 remains open, switch 95 remains closed and switch 94 is closed, thereby permitting the audio signal to pass from the reference power amplifier to the switch 84 without attenuation. Thus, the TEST MODE selector 96 may be positioned to supply a test signal only, a test signal and a low amplitude reference signal, or a test signal and a high amplitude reference signal. As discussed below, the single test signal is used for the threshold test and the test signal and reference signal combination is used for the supra-threshold test, with the amplitude of the reference signal being selected according to the intensity of any ambient noise that may be present in the test environment.

The operation of the signal generating section 40 (FIG. 3b) of the test unit 20 is selectively and automatically regulated by the operation of the signal control section 110 shown in the upper portion of the logic diagram of FIG. 2 and in the schematic diagram of FIG. 3a. Section 110 includes a source of electrical energy, for example the battery pair 112 and 114, that is connected through a service switch 115 mounted on the bottom panel 117 of the test unit enclosure 30 to a main control circuit 116 that controls the operation of the remainder of the section. With switch 115 closed, activation of the main control circuit 116 is accomplished by depressing a START push-button switch 118 mounted on the front panel 32 of the test unit enclosure 30 or by closing the parallel connected toggle switch 120 or push-button switch 121. As the START push-button switch 118, the toggle switch 120 and the push-button switch 121 are electrically equivalent and configured to produce the identical result, the following discussion of the operation of the signal control section 110 refers to the toggle switch only with the understanding that any of the switches 118, 120 or 121 may be employed.

Once the remotely operable toggle switch 120 is closed, a one-shot multi-vibrator 122 included in the main control circuit 116 is set and remains set for a period of time determined by the RC time constant of the resistor 124 and capacitor 126 connected to its R/C and C terminals. The values for resistor 124 and capacitor 126 are selected to ensure that the multi-vibrator 122 will remain set for a period of time sufficient to complete a normal operating cycle of the test unit 20.

The setting of the multi-vibrator 122 causes the following events to occur substantially simultaneously:

1. Logic signals from the Q and Q terminals of the multi-vibrator 122 are fed as shown to the base junctions of transistors 128 and 130 to switch electrical energy from the batteries 112 and 114 to the remainder of the signal control section 110 and to all of the signal generating section 40 by electrically connecting the appropriate terminal of the batteries to each of the arrowheads labeled +6v and −6v in FIGS. 3a and 3b.

2. The Q logic signal of the multi-vibrator 122 is fed to the pre-set (P) input terminal 132 of each of two up/down counter modules 134 and 136. The counter modules are configured as a two-digit, binary coded decimal (BCD) counter with counter module 134 serving as the units counter and counter module 136 serving as the tens counter, and the application of the Q logic signal pre-sets the counters with an initial arbitrary BCD value of 50 as determined by the logic signals continuously present at the logic input terminals 138 of each of the modules. Although the Q logic signal remains steady at the multi-vibrator 122 as long as the multi-vibrator is set, it appears as a momentary pulse at the P terminals of the counter modules because of the action of the capacitor 139 connected in the line 143 between the multi-vibrator 122 and the counter modules 134 and 136. Thus, the Q logic signal is present at the P terminals 132 of the counter modules only for a time sufficient to pre-set the modules to their predetermined initial value. The counter modules employed comprise conventional clock-driven counter circuits that count up or down in one digit steps depending upon the logic signals presented to their respective up/down (U/D)

terminals 135 and carry-in (CI) terminals 137. The units counter module 134 is constantly enabled by the −6 volts at its carry-in terminal 137 and the tens counter module 136 is periodically enabled by a logic signal transmitted from the carry-out (CO) terminal 141 of the counter module 134 each time the latter counter is incremented above a BCD 9 or decremented below a BCD 0. Suitable up/down counter modules are manufactured by RCA under its part No. CD4029.

3. A free-running clock circuit 150 is activated to generate a substantially square-wave signal and transmit the signal to a signal modulation circuit 160. This latter circuit divides the clock signal by four and feeds it to the respective clock (CK) input terminals 139 of the up/down counter modules 134 and 136 after a short initial delay as described below. The signal modulation circuit 160 also generates and feeds a pair of logic signals to the electronic switches 74 and 76 of the signal generating section 40 of FIG. 3b to selectively gate the weighted noise signal from the weighting amplifier 56 as a series of noise pulses through the digitally controlled attenuator 72 to the test signal amplifier 68 and also, whenever switch 89 is in the open position, to the reference signal amplifier 70. The dual J-K flip-flop 162a and b forming the nucleus of the signal modulating circuit 160 (FIG. 3a) is connected such that the electronic switches 74 and 76 are sequentially activated to produce a pulsed test signal and a pulsed reference signal as shown in FIG. 5 such that each pulse has a duration $t_1$ and an interpulse time interval $t_2$, and the two-pulse trains overlap such that each test pulse begins a time $t_3$ after the preceding reference pulse begins and each reference pulse begins when the preceding test pulse ends. Although the circuitry of the signal modulating circuit 160 could be altered to produce pulse trains having various values of $t_1$, $t_2$ and $t_3$, the exemplary apparatus shown in the drawing produces pulses wherein $t_2$ and $t_3$ each equal one-third $t_1$.

4. A second one-shot multi-vibrator 156 is set by the Q signal of the multi-vibrator 122, causing a click suppressor circuit 158 connected across the output terminal of the test signal power amplifier 68, as shown in FIG. 3b, to be momentarily activated to mute the output of the amplifier until the output level of the amplifier has stabilized. The length of time that the multi-vibrator 156 remains set is determined by the RC time constant of the resistor 157 and capacitor 159 connected to its R/C and C terminals and is only as long as necessary to prevent any transient disturbance generated by the closing of switch 120 and the setting of the multi-vibrator 122 from being transmitted through the TEST SIGNAL switch 84 to a transducer 26 of the headphone 22.

Besides setting the multi-vibrator 122, the closing of switch 120 also causes the following events to occur substantially simultaneously:

1. The up/down counter modules 134 and 136 are set to count down by the application of a logical "zero" signal to their respective U/D terminals 135.

2. The same logical "zero" signal is fed to a clock-/counter control circuit where it is converted into a logical "one" pulse by an inverter 145 and capacitor 147 and then fed to the signal modulation circuit 160, to momentarily set the JK flip flop 162a, preventing the clock signal generated by the clock circuit 150 from passing through the modulation circuit and reaching the respective clock (CK) terminals 139 of the two counter modules 134 and 136, thereby stopping the operation of the counter modules until they have been set to count down as described in the preceding paragraph. When the logical "one" pulse from the clock/counter control circuit falls to a "zero," the flip flop 162a is released permitting the clock signal to begin decrementing the counter modules.

As the up/down counter modules 134 and 136 are operating, the logical output signals from each module are fed, as indicated in FIGS. 3a and 3b, in their true and complementary forms to the appropriate electronic switches 78 and 80 of the digitally controlled attenuator 72. Initially, with the counter modules set to a BCD 50, the 10 db and 40 db attenuator segments 75 will be removed from the circuit by the application of a logical "one" to their switches 78 and a logical "zero" to their switches 80. The remaining switches 78 and 80 will all receive a logical "zero" and "one," respectively, with the result that the signal flowing through the attenuator network 72 will be attenuated by 85 minus 50 or 35 db. As the counter modules 134 and 136 count down, less attenuation will be removed from the attenuator network 72 causing the amplitude of the signal leaving the test signal amplifier 68 to decrease by 1 db for each count of the counter. If the remote control switch 120 is opened, as described more fully below, the up/down counters 134 and 136 will count up and the attenuation of the test signal will be sequentially decreased permitting the amplitude of the signal to increase.

The timing relationship between the signal fed to the clock input terminals of the up/down counters 134 and 136 and the signal pair fed to the electronic switches 74 and 76 is such that the counter module 134 is incremented or decremented once for every two pulses of the test signal. In the preferred embodiment, this relationship results in the test signal amplitude being incremented or decremented 1 db each 2 pulses at a rate of 2 db/sec. or 4 pulses/sec. Other timing relationships could be employed as well.

The logical output signals from the up/down counter modules are also fed in their true form to a pair of latch/decoder modules 140 and 142 as shown in FIG. 3a. Each latch decoder module is of a readily available type that receives and decodes a BCD input signal for transmission on demand to a seven-segment display module for subsequent display. One such display module 144 and 146 respectively is connected to the output of each latch/decoder module 140 and 142 and mounted in a visible position on the front panel 32 of the test unit enclosure 30 as shown in FIG. 1. Each time that the remote control switch 120 is opened, as described below, the latch/decoder modules 140 and 142 will decode and transfer to the display modules the last BCD value generated by the up/down counter modules 134 and 136. By using the same set of signals to both control the attenuator network 72 and drive the display modules 144 and 146, a digital display representative of the relative amplitude of the test signal is generated without the need to convert the analog value of the test signal amplitude into a digital form. Suitable latch/decoder modules are manufactured by RCA under its part number CD4511B.

A battery test circuit 164 is included in the signal control section 110 of FIG. 3a to provide an indication, through the display modules 144 and 146, of the electrical energy remaining in the batteries 112 and 114. When the battery test switch 166 mounted on the bottom panel 117 of the test unit enclosure 30 is depressed, a DC voltage proportional to the current flowing through the Zener diode 44 is fed through the battery test circuit 164 to the light test input terminals 167 of each of the latch/decoder modules 140 and 142 causing the latch/decoder modules to drive all seven segments of each display module 144 and 146 and thereby produce a decimal display of the number 88. The activation of all segments of each display module 144 and 146 produces the greatest drain upon the batteries 112 and 114. If the energy remaining in the batteries is sufficient both to drive the Zener diode 44 into breakdown and also to maintain a display of a decimal 88, then the batteries are considered sufficient to operate the entire circuitry. If the energy remaining in the battery is not sufficient to produce the display of a decimal 88, the batteries should be recharged or removed and replaced. An operator alarm circuit 192 is also provided, as shown in FIG. 3a, to signal the test unit operator whenever a value is being displayed by the display modules 144 and 146 that should be recorded or otherwise noted.

In operation to perform the previously-described threshold test, the earcups of the headphone 22 are placed over the ears of the subject individual as shown in FIG. 1 without disturbing the placement of the earplugs 180 fitted into the subject's ear canals 181, the TEST SIGNAL switch 84 of the test unit 20 is placed in the L position, and the TEST MODE switch is placed in the THRESH (QUIET) position. The test unit is then activated by depressing either the push-button START switch 118 or the remote push-button switch 121 to set the multi-vibrator 112 of the main control circuit. Although the electrically equivalent remote toggle switch 120 could be employed as well it has been found that accurate and consistent subject response is more easily obtained in the threshold test if the subject is directed to use the remote push-button switch 121.

The setting of the multi-vibrator 122 causes power to be supplied from the batteries 112 and 114 to the remainder of the circuitry within the test unit and also initializes the up/down counters 134 and 136 to their pre-set value of 50. At the same time, the power supplied to the signal producing section 40 of the test unit 20 causes the noise generator 42 and the weighting amplifier 56 to produce the complex weighted test signal that is fed through the digitally controlled amplifier 72 and test signal power amplifier 68 to the left transducer 26 of the headphone 22. The test signal, as it is fed through the digitally controlled attenuator 72, is attenuated an initial 35 db to a comfortably audible level by the effective removal from the attenuator network of the 40 db and 10 db attenuator segments that are controlled respectively by the BCD 40 and BCD 10 logic lines from the up/down counter 136. The level adjuster 82 may be adjusted to ensure that the initial amplitude of the test signal is indeed comfortably audible, but once set, the level adjuster should not be disturbed for the duration of the test. As long as switch 121 remains closed, the two counter modules 134 and 136 will automatically decrement. While the counters are decrementing, the appropriate attenuator segments 75 of the digitally controlled attenuator circuit 72 are selected and deselected to attenuate the amplitude of the test signal in steps of one db for each count of the counters. The clock circuit 150 also drives the signal modulating circuit 160 to selectively activate the electronic switch 74 and pulse the test signal as shown in FIG. 5.

The operation of the test unit circuitry will continue thusly until either switch 121 is opened or the counter modules 134 and 136 have decremented below a BCD value of zero. The first number below zero in a two-digit BCD counter is 99 and when that number is reached, the BCD 80 output terminal of counter module 136 will be activated and a corresponding signal fed to the reset terminal of multi-vibrator 122, as shown in FIG. 3a, causing the multi-vibrator to reset to its initial state, thereby removing power from the remainder of the test unit circuitry.

Normally, before the up/down counter modules 134 and 136 have decremented from their initial BCD value of 50 to a BCD value below zero, the amplitude of the test signal supplied to the selected transducer 26 will have been attenuated to a level that is inaudible to the subject. At that point, per previous instruction, the subject will release the push-button switch 121. When the push-button switch 121 is opened, the latch/decoder modules 140 and 142 are activated to decode and transmit the last logical values produced by the counter modules 134 and 136 to the display modules 144 and 146 for display. At the same time, a signal generated by the clock/counter control circuit 148 activates an alarm circuit 192 thereby energizing an alarm 194 to produce a short audible signal as an indication to the test unit operator that note should be taken of the numerical value displayed by the display modules, that value being representative of the test signal amplitude which is barely inaudible to the subject. The test may then be terminated by depressing the STOP pushbutton 196 mounted on the front panel 32 of the test unit enclosure 30 to reset the multi-vibrator 122 to its initial or cleared state.

It should be noted that even though the counter modules 134 and 136 were started at an initial arbitrary value of 50 and the numerical representation displayed by the display modules 144 and 146 of the amplitude of the test signal is therefore not related to any standard scale and consequently fictitious, the difference between any two numerical representations displayed by the display modules is still an accurate indication of the difference between two amplitudes of the test signal and that difference is the same as would be measured with reference to a standard scale.

Normally, rather than depressing the STOP pushbutton 196 to clear the multi-vibrator 122, the test will be continued as the subject releases the push-button switch 121 to its open position, thereby switching the up/down signal supplied to the counter module 134 and 136 to a logical zero causing the counter modules to be set to count up. The opening of the push button switch 121 also causes the clock/counter control circuit 148 to transmit a logical "one" via the JK flip flop 162a to the respective CK terminals of the counter modules 134 and 136 for a period of time sufficient to permit the up/down counter modules to stabilize before actually beginning to increment. The flip flop 162a is then released and the counter modules are permitted to increment at the same predetermined rate that they were previously decremented. The incrementing counter modules in turn select and deselect the appropriate segments 75 of the digitally controlled attenuator 72, causing the amplitude of the test signal to be incremented in one db steps. If no further action is taken by the subject, the counter modules 134 and 136 will continue to increment until their combined value has increased to 80. When the counter modules 134 and 136 reach that value, the BCD 80 terminal of counter module 136 will again be activated, sending a signal to the reset terminal of the multi-vibrator 122 to shut down the test unit. Before this happens, the subject, per previous instruction, will redepress the remote control push-button switch 121 to its closed position at the point where the amplitude of the test signal again becomes just barely audible. To facilitate the operation of the push-button switch 121 and to prevent its being left in a closed position, the switch may be spring-biased toward its open position.

With the push-button switch 121 again closed, the amplitude of the test signal will be decremented as before until it is no longer audible to the subject individual, at which time the push-button switch 121 is opened, the display modules 144 and 146 will display the value contained in the up/down counter modules 134 and 136 and the operator alarm circuit 192 will be activated. In this manner, a plurality of numerical representations of the test signal amplitude which is barely inaudible to the subject may be noted and recorded by the test unit operator.

To perform the threshold test with a test signal transmitted to the subject individual's right ear, the TEST SIGNAL switch 84 is repositioned to its opposite or R position and the above procedure repeated.

In operation to perform the previously described supra-threshold test, the TEST MODE switch 96 of the test unit 20 is positioned to either the SUPRA (HI) or SUPRA (LO) position and the toggle switch 120 moved to its closed position indicated by the downwardly pointing arrow symbol 123 of the remote control unit 24. It has been found that the use of a toggle switch in the supra-threshold test, as opposed to a push-button switch, is especially advantageous for ease of subject response. The only change in the operation of the test unit circuitry with the TEST MODE switch in either of the SUPRA positions is that the signal from the signal weighting amplifier 56, besides being fed through the digitally controlled attenuator 72 to the test signal power amplifier 68 is also fed to the reference signal power amplifier 70, and both the test signal and the reference signal will be pulsed by the reciprocating operation of the two electronic switches 74 and 76 to produce the two time-spaced pulsed trains of FIG. 5. The toggle switch should be held by the subject in such an orientation that the closed position is toward the ear being tested and the open position is toward the ear receiving the reference signal, as this facilitates operation by the subject who can then be instructed simply to move the switch in the direction of the ear in which the loudest sound is perceived.

As the amplitude of the test signal is being automatically attenuated under the control of the up/down counter modules 134 and 136, the subject will be listening for the point where the test signal has a predetermined relationship to the reference signal as described earlier. When that point is reached, the individual repositions the remote control toggle switch 120, by moving it toward the upwardly directed arrow symbol 125 of the remote control unit 24, causing the last value in the up/down counter modules 134 and 136 to be displayed by the display modules 144 and 146 and the alarm 194 to sound. If the test mode switch 94 is positioned in the SUPRA (HI) position, the reference signal will be transmitted to the subject at a higher amplitude than if the TEST MODE switch 96 is positioned in the SUPRA (LO) position. As before, the initial amplitude of the reference signal may be varied by adjusting the level adjuster 90. In all other respects the operation of the test unit circuitry is identical to that described above for the threshold test.

In an alternate embodiment of the apparatus of the present invention, the digitally controlled attenuator 72 is replaced by a manually variable attenuator 200 of any conventional type as indicated by the block diagram of FIG. 6. With this embodiment, the amplitude of the test signal generated by the noise generator 42 and weighted by the weighting amplifier 56, rather than being automatically decremented and incremented under the control of a counter circuit, is manually adjustable by varying the attenuator 200. An indicator 202 coupled to the variable attenuator 200 provides a continuous indication of the setting of the attenuator, and thereby the amplitude of the test signal. This indicator 202 may be electrical, either analog or digital, or it may be mechanized. Indicator adjusting means 204 associated with the indicator 202 permits the indicator to be adjusted to any desired reference value regardless of the actual setting of the attenuator 200.

In operation, for example to perform the abovedescribed threshold test, the headphone 22 is placed in position as before over the ears of a subject with earplugs in place, the apparatus is activated and set to transmit the test signal through the variable attenuator 200 to the selected test ear, and the attenuator is manually adjusted either by the test operator or by the subject until the test signal is just barely inaudible (or audible) to the subject through the earplug in place in the test ear. The indicator 202 is then re-set by manipulating the indicator adjusting means 204 to a convenient reference value, for example zero, the earplug is removed from the test ear, and the attenuator 200 again manually adjusted until the test signal is perceived at the same level, at which point the indicator 202 will indicate directly the difference between the amplitudes of the test signal at the two levels with the earplug in place and with the earplug removed respectively. Preferably, the indicator 202 is calibrated in decibels, thereby providing a direct indication of the acoustical attenuation effectiveness of the removed earplug. Operation of the alternate embodiment to perform the supra-threshold test should be apparent without further explanation.

The terms and expressions which have been employed in the foregoing abstract and specification are used therein as terms of description and not of limitation, and there is no intention, in the use of such terms and expressions, of portions thereof, it being recognized that the scope of the invention is defined and limited only by the claims which follow.

What is claimed is:

1. A method of measuring, in the presence of significant ambient noise, the acoustical attenuation effectiveness of a hearing protector worn in operative association with an ear by a subject individual, said method comprising the steps of:
  a. generating a variable-amplitude audio signal and a separate audio signal of a constant amplitude sufficiently great to be audible to said individual over said ambient noise;
  b. exposing said ear to one of said signals with said hearing protector worn in association with said ear, and without said hearing protector being so worn, respectively;
  c. during the exposure of said ear to said signal, exposing the other ear of said individual to the other of said audio signals;
  d. varying said variable signal both with and without said hearing protector being so worn until obtaining in each instance an indication from said individual that he perceives that said variable signal has a predetermined common relationship to said constant-amplitude signal; and e. measuring the difference between the respective amplitudes of said variable signal which are indicated in each instance by said individual as having said predetermined relationship to said constant-amplitude signal.

2. The method of claim 1 including the step of generating said constant-amplitude signal in a form which is audibly distinguishable from said variable signal other than with respect to amplitude.

3. The method of claim 2 including the step of generating said constant-amplitude signal and said variable signal respectively as pulses audibly distinguishable with respect to time.

4. The method of claim 1 including the step of generating said constant-amplitude signal and said variable signal respectively each as periodic pulses having asymmetrical time sequences, a portion of a pulse of said constant-amplitude signal occurring during a portion of a pulse of said variable signal.

5. The method of claim 1, further including repeating step (d) a plurality of times and averaging the amplitude differences obtained from only certain ones of said indications by said individual which occur after the first indication with and without said hearing protector respectively, the resultant averaged amplitude difference being the acoustical attenuation of said hearing protector.

* * * * *

UNITED STATES PATENT AND TRADEMARK OFFICE
CERTIFICATE OF CORRECTION

PATENT NO. : 4,060,701
DATED : November 29, 1977
INVENTOR(S) : John M. Epley

It is certified that error appears in the above-identified patent and that said Letters Patent are hereby corrected as shown below:

Col. 8, line 52   Delete the word "METHOD";

line 53   Add the word --Method-- (centered).

Col. 9, line 24   After "becomes" add the word --barely--.

Col. 14, line 56   After "Thus," add the word --in--.

Col. 20, line 27   Change "pushbutton" to --push-button--.

Col. 22, line 19   Change "abovedescribed" to --above-described--.

Signed and Sealed this

Fifteenth Day of August 1978

[SEAL]

Attest:

RUTH C. MASON
Attesting Officer

DONALD W. BANNER
Commissioner of Patents and Trademarks